US012629435B2

(12) United States Patent
Childress

(10) Patent No.: US 12,629,435 B2
(45) Date of Patent: May 19, 2026

(54) SANITIZING SYSTEM

(71) Applicant: THE BOEING COMPANY, Chicago, IL (US)

(72) Inventor: Jamie J. Childress, Mercer Island, WA (US)

(73) Assignee: The Boeing Company, Arlington, VA (US)

( * ) Notice: Subject to any disclaimer, the term of this patent is extended or adjusted under 35 U.S.C. 154(b) by 1026 days.

(21) Appl. No.: 17/352,852

(22) Filed: Jun. 21, 2021

(65) Prior Publication Data

US 2021/0393824 A1     Dec. 23, 2021

Related U.S. Application Data

(60) Provisional application No. 63/042,904, filed on Jun. 23, 2020.

(51) Int. Cl.
*A61L 2/10* (2006.01)
*A61L 2/24* (2006.01)
(Continued)

(52) U.S. Cl.
CPC *A61L 2/10* (2013.01); *A61L 2/24* (2013.01); *A61L 2/26* (2013.01); *B64D 47/02* (2013.01);
(Continued)

(58) Field of Classification Search
CPC ..... A61L 2/10; A61L 2/24; A61L 2/26; A61L 2202/11; A61L 2202/14; A61L 2202/25;
(Continued)

(56) References Cited

U.S. PATENT DOCUMENTS 10,130,727 B1     11/2018  Byrnes et al.
2007/0053188 A1    3/2007  New
(Continued)

FOREIGN PATENT DOCUMENTS

DE      2020001197      4/2020
EP      3293118        3/2018
(Continued)

OTHER PUBLICATIONS

Extended European Search Report for EP 2118083.3-1010, dated Nov. 3, 2021.
(Continued)

*Primary Examiner* — Brendan A Hensel
(74) *Attorney, Agent, or Firm* — Joseph M. Butscher; Carroll, Hoette & Butscher, LLC

(57)     ABSTRACT

A sanitizing system includes a plurality of ultraviolet (UV) lamps and a control unit that includes one or more processors. The UV lamps are mounted at various locations within an internal cabin of a vehicle. The UV lamps are configured to receive electrical power from a power source onboard the vehicle and to emit UV light into the internal cabin during a trip of the vehicle. The control unit is operatively connected to the UV lamps and configured to modify the electrical power supplied to one or more of the UV lamps located in a common area of the internal cabin based on occupancy of the common area.

19 Claims, 7 Drawing Sheets

(51) Int. Cl.

| | | |
|---|---|---|
| *A61L 2/26* | (2006.01) |
| *A61L 103/75* | (2026.01) |
| *B64D 47/02* | (2006.01) |
| *B64F 5/30* | (2017.01) |

(52) U.S. Cl.
CPC ............. *B64F 5/30* (2017.01); *A61L 2103/75* (2026.01); *A61L 2202/11* (2013.01); *A61L 2202/14* (2013.01)

(58) Field of Classification Search
CPC ..... A61L 9/20; A61L 2209/111; B64D 47/02; B64F 5/30
See application file for complete search history.

(56) References Cited

U.S. PATENT DOCUMENTS

| | | | |
|---|---|---|---|
| 2016/0000951 A1 | 1/2016 | Kreiner | |
| 2016/0089459 A1 | 3/2016 | Boodaghians | |
| 2017/0080117 A1 | 3/2017 | Gordon | |
| 2017/0284076 A1* | 10/2017 | Jensen | .................... E03D 9/002 |
| 2018/0055959 A1 | 3/2018 | Lin | |
| 2018/0369434 A1 | 12/2018 | Callahan | |
| 2019/0030195 A1 | 1/2019 | Hatti | |
| 2020/0164988 A1 | 5/2020 | Alvarez | |
| 2021/0018884 A1* | 1/2021 | Kupa | ................... H05B 47/115 |
| 2022/0323624 A1* | 10/2022 | Igarashi | ................... A61L 2/24 |
| 2023/0130283 A1* | 4/2023 | Naito | ....................... A61L 2/10 |
| | | | 422/3 |

FOREIGN PATENT DOCUMENTS

| | | |
|---|---|---|
| EP | 3659919 | 6/2020 |
| JP | 2018-69028 | 5/2018 |
| JP | 2018-69029 | 5/2018 |

OTHER PUBLICATIONS

Welch David et al: "Far-UVC Light: A New Tool to Control the Spread of Airborne Mediated Microbial Diseases", Scientific Reports, vol. 8, No. 2752 (Dec. 1, 2018), pp. 1-7.
English version of JP 2018-69028.
English version of JP 2018-69029.

* cited by examiner

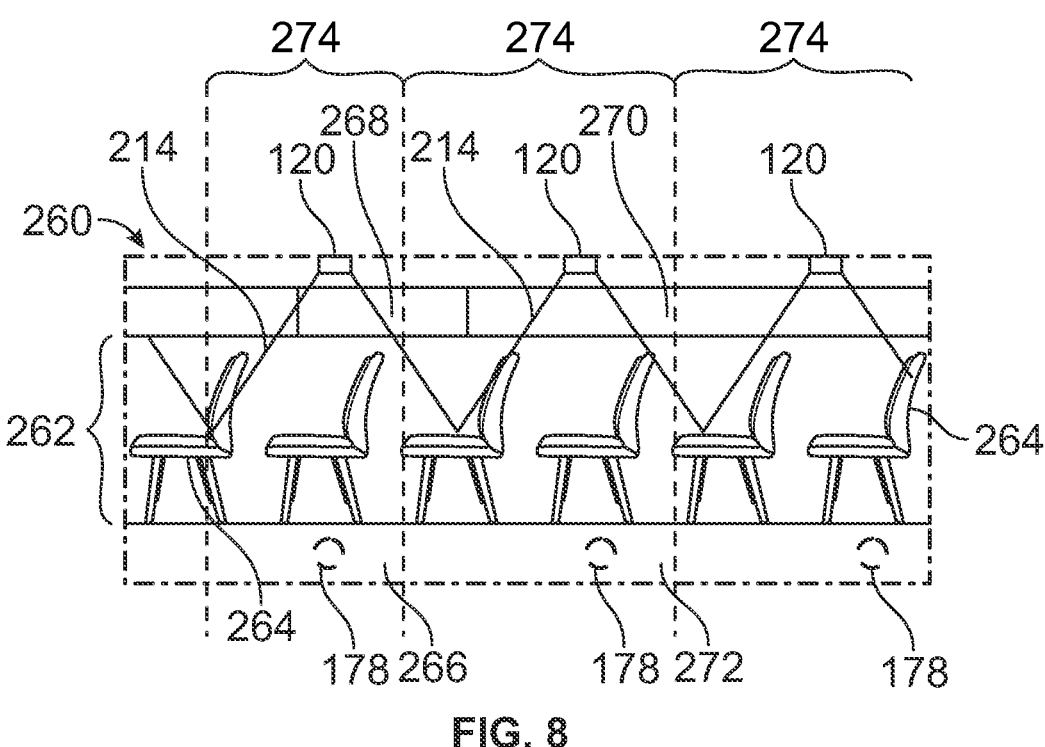
FIG. 8
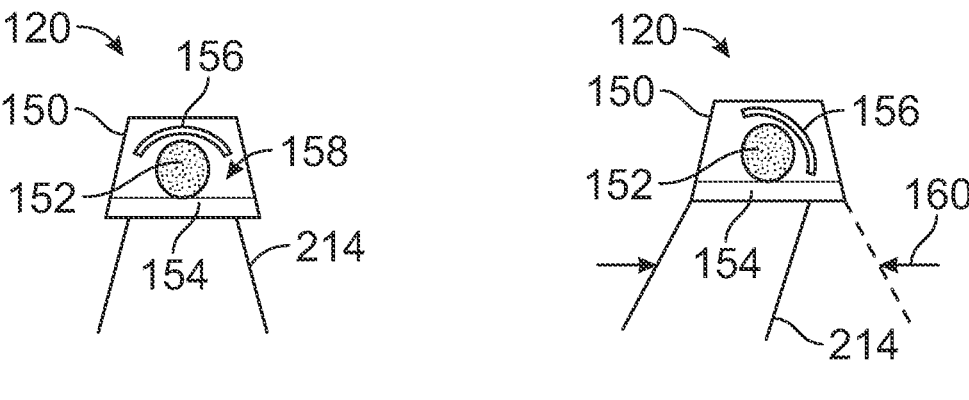
FIG. 9          FIG. 10

SANITIZING SYSTEM

CROSS-REFERENCE TO RELATED APPLICATIONS

This application relates to and claims priority benefits from U.S. Provisional Patent Application No. 63/042,904, filed 23 Jun. 2020 and entitled "Sanitizing System," which is hereby incorporated by reference in its entirety.

FIELD OF THE DISCLOSURE

Embodiments of the present disclosure generally relate to systems and methods that may be used to sanitize structures and air within enclosed structures, such as vehicle cabins.

BACKGROUND OF THE DISCLOSURE

Vehicles such as commercial aircraft are used to transport passengers between various locations. Systems are currently being developed to disinfect or otherwise sanitize surfaces to kill or neutralize various harmful microbes or other pathogens. Typical methods of sanitizing surfaces within aircraft involve significant manual effort by one or more crew members. For example, some crew members may spray and wipe cleaning chemicals on surfaces within an internal cabin of the aircraft. Other crew members may slowly wave a wand that emits ultraviolet (UV) radiation on nearby surfaces of the internal cabin. The UV radiation can kill or neutralize some microbes or other pathogens if held at a certain proximity to a target surface for at least a designated amount of time.

Furthermore, many commercial vehicles such as aircraft have HEPA filters in the air conditioning system that are able to entrap microbes and pathogens. The HEPA filters receive and clean air exiting the cabin or about to enter the cabin. HEPA filters and frequent cleaning of the cabin between flights are some methods to ensure the health of the passengers and crew onboard the aircraft. Additional sanitizing methods could be used to supplement the HEPA filters and chemical cleanings.

SUMMARY OF THE DISCLOSURE

A need exists for a system and a method for prohibiting the spread of pathogens between passengers onboard a vehicle during a trip, such as between passengers in an internal cabin of an aircraft during a flight, without risking harm to the passengers.

With those needs in mind, certain embodiments of the present disclosure provide a sanitizing system that includes a plurality of ultraviolet (UV) lamps and a control unit that includes one or more processors. The UV lamps are mounted at various locations within an internal cabin of a vehicle. The UV lamps are configured to receive electrical power from a power source onboard the vehicle and to emit UV light into the internal cabin during a trip of the vehicle. The control unit is operatively connected to the UV lamps and configured to modify the electrical power supplied to one or more of the UV lamps located in a common area of the internal cabin based on occupancy of the common area.

In one or more embodiments, a method for sanitizing a vehicle is provided. The method includes supplying electrical power from a power source onboard a vehicle to a plurality of ultraviolet (UV) lamps mounted at various locations within an internal cabin of the vehicle for the UV lamps to emit UV light into the internal cabin during a trip of the vehicle. The method also includes modifying the electrical power supplied to one or more of the UV lamps located in a common area of the internal cabin based on occupancy of the common area.

In one or more embodiments, a sanitizing system is provided that includes a plurality of ultraviolet (UV) lamps, one or more sensors, and a control unit that includes one or more processors. The UV lamps are mounted at various locations within an internal cabin of a vehicle. The UV lamps are configured to receive electrical power from a power source onboard the vehicle and to emit UV light into the internal cabin during a trip of the vehicle at a designated wavelength or narrow wavelength range that is safe for human tissue. The one or more sensors are mounted within the internal cabin and configured to monitor a common area of the internal cabin. The control unit is operatively connected to the UV lamps and the one or more sensors. The control unit is configured to determine an occupancy of the common area based on signals received from the one or more sensors and to modify the electrical power supplied to one or more of the UV lamps located in the common area based on the determined occupancy of the common area.

BRIEF DESCRIPTION OF THE DRAWINGS

FIG. 8 illustrates a side view of a passenger seating area of an internal cabin showing a group of passenger seats on one side of an aisle.

FIG. 9 illustrates a side view of one UV lamp of the sanitizing system according to an embodiment.

FIG. 10 illustrates a side view of the UV lamp of the sanitizing system according to another embodiment.

DETAILED DESCRIPTION OF THE DISCLOSURE

Figure 1:
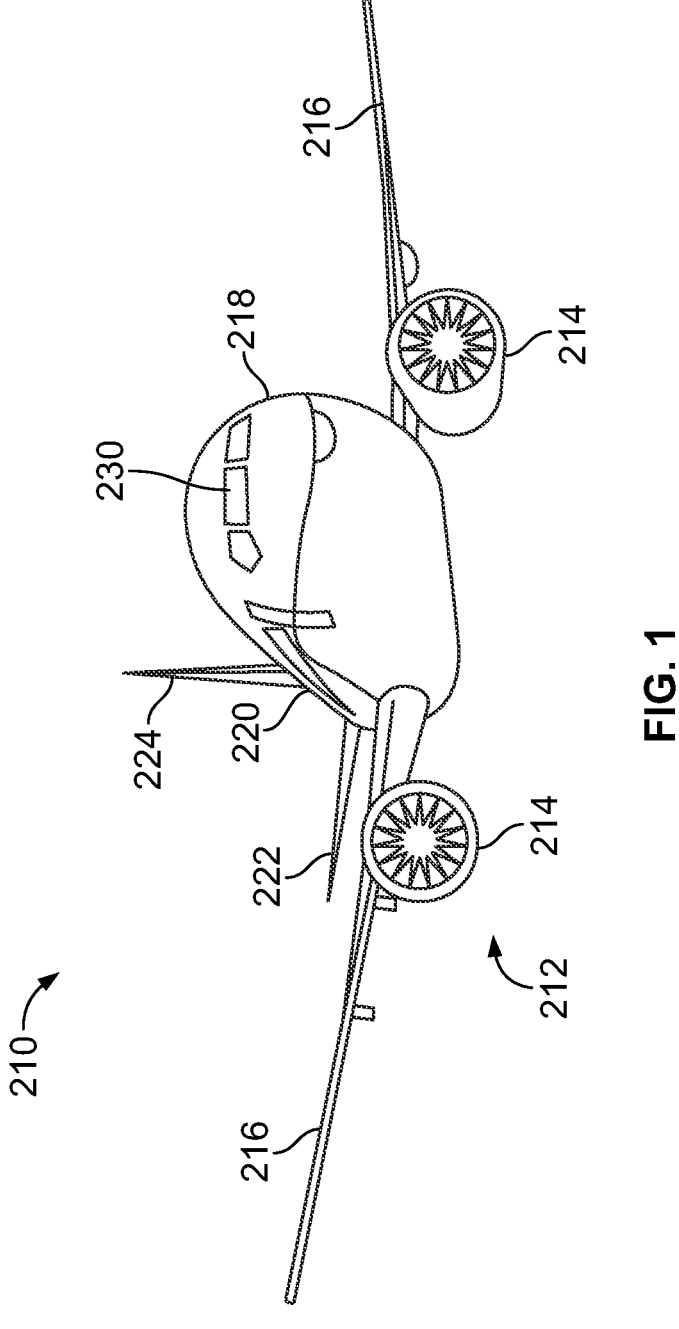
FIG. 1 illustrates a perspective front view of an aircraft, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system and method for disinfecting the internal cabin of a vehicle, such as a commercial aircraft. The sanitizing system includes a group of ultraviolet (UV) lamps arranged within the internal cabin. The UV lamps are positioned and controlled to emit UV light into the internal cabin during travel of the vehicle such that the UV light sanitizes air and surfaces within the internal cabin. The UV lamps may be controlled to emit filtered UV light at a designated wavelength or narrow wavelength range that is safe for human tissue. For example, the designated wavelength may be 222 nm. The UV lamps are positioned to sanitize air and surfaces before the air and surfaces can be cleaned via air filtering (e.g., with HEPA filters) and manual application of chemical cleaners. At least some of the UV lamps may be operated to persistently emit UV light for extended periods of time. For example, at least some of the UV lamps may be on (e.g., active) to continuously emit UV light throughout an entire duration of a trip, from the time that passengers board the vehicle to the time that passengers deboard. The persistent UV emission kills or neutralizes pathogens to prohibit the spread of pathogens in the air and on surfaces during travel of the vehicle, between cabin cleanings and air conditioning cycles.

In embodiments disclosed herein, at least some of the UV lamps are located in areas of the internal cabin that are available for use by more than one person, even if not at the same time. Such areas are referred to herein as common areas. As opposed to the areas around passenger seats, which are only available to a single person, the common areas are shared between multiple passengers and/or crew members. The common areas can include lavatories, aisles, vehicle entrance areas, vehicle exit areas (if different from the entrance areas), galleys, areas outside lavatories, crew quarters, suites for first-class passengers, and the like. As used herein, the common areas do not refer to general passenger seating areas, such as coach seating, although can refer to an aisle that extends through general passenger seating areas because the aisle is used by multiple passengers and crew members. The UV lamps located in the common areas emit UV light to sanitize and disinfect the common areas. The common areas may have intermittent occupation. For example, during takeoff and landing of an aircraft, the passengers and crew remain seated so at least some of the common areas may be unoccupied.

The sanitizing system disclosed herein controls the operation of the UV lamps within the common areas based on occupancy of the common areas. For example, the UV lamps may receive greater electrical power when the associated common area is occupied or immediately after the common area is occupied, than when the associated common area is unoccupied for an extended period of time. The receipt of greater electrical power causes the UV lamps to emit UV light at a greater intensity and/or range within a field of illumination, which can kill or neutralize a greater amount or percentage of pathogens per unit time than UV light having a lower intensity caused by operating the UV lamps at a reduced power level. The high intensity of the UV light at the greater electrical power can be used to rapidly sanitize the common area. For example, the common area can be rapidly sanitized on an interval time basis or on an occupant basis, such that the rapid sanitization occurs during or after each occupant in the common area. When the common area is unoccupied, the electrical power to the UV lamps in the common area can be reduced or even cut off to conserve electrical energy relative to operating the UV lamps in the common area at a high power level or setting for the entire trip or at least an extended period of time. Therefore, the power supplied to the UV lamps in the common areas can be selectively modulated or modified based on occupancy to provide rapid sanitization when desired while limiting the consumption of electrical power.

Occupancy as referred to herein refers to whether or not at least one person is present in a designated area, and therefore is generally referred to in the binary sense. The sanitization system may detect that an area is occupied without necessarily determining additional information, such as the number of persons or identity of the persons present in the area. An occupant to a common area can refer to any person, such as a passenger or a crew member. In the embodiments described herein, the sanitizing system controls the UV lamps located in common areas in different modes or settings based on the occupancy status of the common areas.

One or more technical effects of the sanitizing system include reducing the spread of pathogens between occupants (e.g., passengers and crew members) of a vehicle during a trip of the vehicle, both through the air and on surfaces. For example, the sanitizing system can rapidly sanitize the air and surfaces in a common area between occupants, such that pathogens emitted from a prior occupant in the common area are killed or neutralized prior to or during a subsequent occupant being present in the common area. Another technical effect is that the presence and operation of the sanitizing system does not negatively impact the health or trip enjoyment of the passengers, as the filtered UV light emitted by the sanitizing system is not distracting or harmful to the passengers. Furthermore, although operating the UV lamps requires energy from a power supply, the sanitizing system can modulate the settings of the UV lamps based on occupancy to reduce the total energy consumed (relative to perpetually operating at a medium or high power setting), which desirably limits power consumption without sacrificing passenger health and safety. The sanitizing system may ensure compliance with regulations that require a safe environment within the cabin of the aircraft during a flight.

FIG. 1 illustrates a perspective front view of an aircraft 10, according to an embodiment of the present disclosure. The aircraft 10 includes a propulsion system 12 that includes engines 14, for example. Optionally, the propulsion system 12 may include more engines 14 than shown. The engines 14 are carried by wings 16 of the aircraft 10. In other embodiments, the engines 14 may be carried by a fuselage 18 and/or an empennage 20. The empennage 20 may also support horizontal stabilizers 22 and a vertical stabilizer 24.

The fuselage 18 of the aircraft 10 defines an internal cabin, which includes a flight deck or cockpit, one or more work sections (for example, galleys, personnel carry-on baggage areas, and the like), one or more passenger sections (for example, first class, business class, and coach sections), one or more lavatories, and/or the like.

Alternatively, instead of an aircraft, embodiments of the present disclosure may be used with various other vehicles, such as automobiles, buses, rail vehicles, watercraft, and the like. For example, the sanitizing system disclosed herein can be implemented in an internal cabin of a passenger train, a bus, a passenger boat, and the like. Embodiments of the present disclosure may also be used with respect to enclosed areas within fixed structures, such as commercial and residential buildings. For example, the sanitizing system and method disclosed herein can be installed and operated within theatres, concert venues, places of worship, office buildings, stores, and the like, where persistent UV light at non-harmful wavelengths can provide continuous disinfection of air and surfaces.

Figures 2A, 2B:
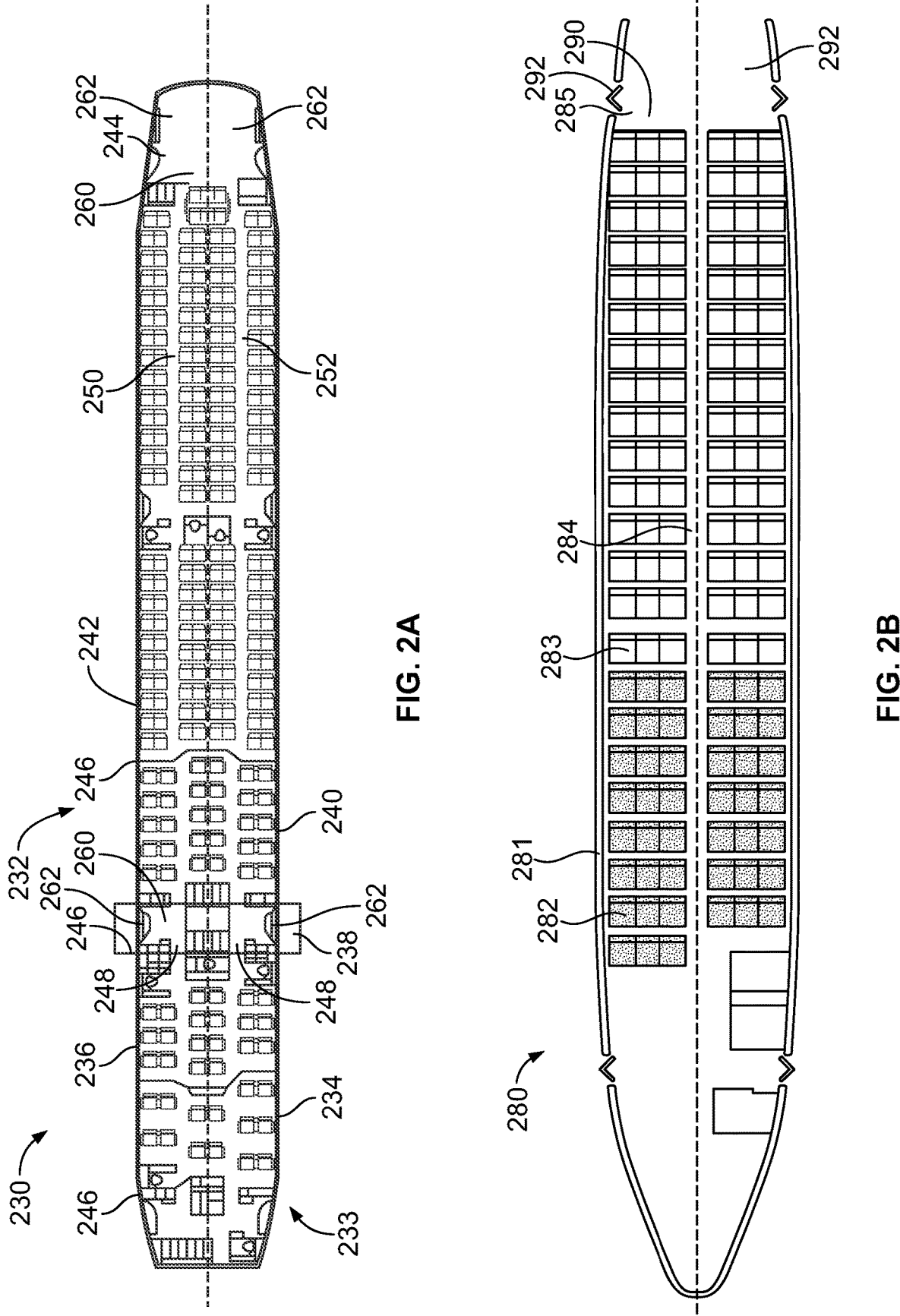
FIG. 2A illustrates a top plan view of an internal cabin of an aircraft, according to an embodiment of the present disclosure.
FIG. 2B illustrates a top plan view of an internal cabin of an aircraft, according to another embodiment of the present disclosure.

FIG. 2A illustrates a top plan view of an internal cabin 30 of an aircraft, according to an embodiment of the present disclosure. The internal cabin 30 may be within the fuselage 18 of the aircraft 10 shown in FIG. 1. For example, one or more fuselage walls may define the internal cabin 30. The internal cabin 30 includes multiple sections, including a front section 33, a first-class section 34, a business class section 36, a front galley station 38, an expanded economy or coach section 40, a standard economy of coach section 42, and an aft section 44. The internal cabin 30 also includes multiple lavatories 45. It is to be understood that the internal cabin 30 may include more or less sections than shown. For example, the internal cabin 30 may not include a first-class section, and may include more or less galley stations than shown. Each of the sections may be separated by a cabin transition area 46, which may include class divider assemblies 48.

As shown in FIG. 2A, the internal cabin 30 includes two aisles 50 and 52 that extend a substantial length of the internal cabin 30 and lead to the aft section 44. The aisles 50 and 52 extend to egress paths or door passageways 60. Exit doors 62 are located at ends of the egress paths 60. The egress paths 60 may be perpendicular to the aisles 250 and 252. The internal cabin 30 may include more egress paths 60 at different locations than shown. Optionally, the internal cabin 30 may have less or more aisles than shown. For example, the internal cabin 30 may include a single aisle that extends through the center of the internal cabin 30 that leads to the aft section 44. The sanitizing system described herein may be used to sanitize air and various structures within the internal cabin 30.

FIG. 2B illustrates a top plan view of an internal cabin 80 of an aircraft, according to another embodiment of the present disclosure. The internal cabin 80 may be within the fuselage 18 of the aircraft 10 shown in FIG. 1. For example, one or more fuselage walls may define the internal cabin 80. The internal cabin 80 includes multiple sections, including a main cabin 82 having passenger seats 83 and an aisle 84, and an aft section 85 behind the main cabin 82. The internal cabin 80 also includes a lavatory 87. The internal cabin 80 may include more or less sections than shown.

The internal cabin 80 has a single aisle 84 that extend a substantial length of the internal cabin 80 and lead to the aft section 85. The aisle 84 may extend through the center of the internal cabin 80 such that the aisle 284 is coaxial with a central longitudinal plane 86 of the internal cabin 80. The aisle 84 extends to egress paths or door passageways 90, which are areas adjacent to entrances of the aircraft. Exit doors 92 are located at ends of the egress paths 90. The egress paths 90 may be perpendicular to the aisle 84. The sanitizing system described herein may be used to sanitize air and various structures within the internal cabin 80.

Figure 3:
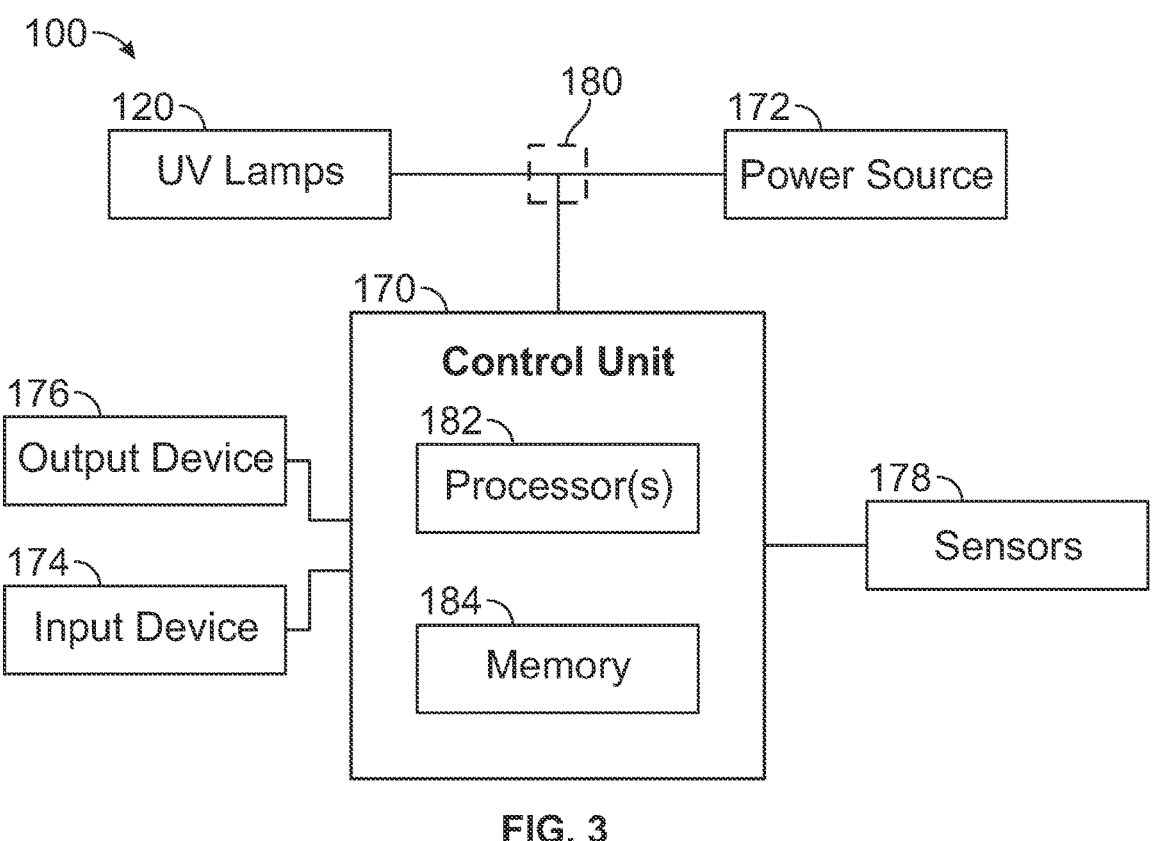
FIG. 3 is a schematic diagram of a sanitizing system according to an embodiment.

FIG. 3 is a schematic diagram of a sanitizing system 100 according to an embodiment. The sanitizing system 100 includes a plurality of ultraviolet (UV) lamps 120 mounted within an internal cabin of a vehicle, such as the cabin 30 shown in FIG. 2A or the cabin 80 shown in FIG. 2B. The UV lamps 120 are controlled to generate and emit UV light into the internal cabin to sanitize and disinfect air and surfaces within the internal cabin. The UV lamps 120 may include excimer bulbs. The UV lamps 120 may be located at various areas throughout the internal cabin. For example, some UV lamps 120 may be located near passenger seats and positioned to emit UV light in respective fields of illumination that encompasses passengers sitting in the seats. Other UV lamps 120 may be located in common areas, such as lavatories, aisles, galleys, ingress and egress pathways, and the like. The sanitizing system 100 is configured to persistently operate at least some of the UV lamps 120 in the on, emitting state even in the presence of passengers, such as during boarding, taxiing, flight, and deboarding. Unlike current practices which only provide intermittent disinfection, such as chemically cleaning the cabin between flights and filtering a given volume of air every time that volume of air is pulled through a return register of an environmental control system, the sanitizing system 100 disinfects pathogens on surfaces and in the air on a continuous basis. The sanitizing system 100 may also provide repetitive, rapid sanitizing of some highly-trafficked common areas based on occupation of the common areas.

The sanitizing system 100 includes the UV lamps 120, a control unit 170, a power source 172, an input device 174, an output device 176, and sensors 178. The sanitizing system 100 is disposed onboard a vehicle, such as the aircraft 10 shown in FIG. 1, or within an enclosed space of a stationary building or structure. The power source 172 provides electrical power to the UV lamps 120 to power the generation of UV light. The power source 172 may be a generator that converts mechanical energy to electrical energy. Various electrically conductive wires and cables may conduct the electrical power from the power source 172 to the UV lamps 120. For example, the UV lamps 120 may utilize the same power source 172 and conductive pathways that supply power to other components in the cabin, such as to personal lights and personal air blowers in passenger service units (PSUs), cabin lighting, and appliances in galleys. For example, the UV lamps 120 may plug into the same electronics package that controls cabin lighting.

The control unit 170 is operatively connected to the UV lamps 120, the input device 174, the output device 176, and the sensors 178 via wired and/or wireless communication pathways. The control unit 170 generates control signals that control the operations of the UV lamps 120. The control signals that are generated may be based on signals (e.g., data) received from the sensors 178. The control unit 170 represents hardware circuitry that includes and/or is connected with one or more processors 182 (e.g., one or more microprocessors, integrated circuits, microcontrollers, field programmable gate arrays, etc.). The control unit includes and/or is connected with a tangible and non-transitory computer-readable storage medium (e.g., memory) 184. For example, the memory 184 may store programmed instructions (e.g., software) that is executed by the one or more processors 182 to perform the operations of the control unit 170 described herein.

The control unit 170 can control the UV lamps 120 by controlling the presence and amount of electrical power (e.g., voltage and current) that is supplied to each of the UV lamps 120. Optionally, the control unit 170 is operatively connected to at least one switching device 180 along the circuit or bus between the power source 172 and the UV lamps 120. The switching device 180 is configured to selectively open (or break) a circuit to block power conduction to one or more of the UV lamps 120 and close (or establish) a circuit to enable power conduction to the one or more UV lamps 120. The switching device 180 may represent or include a solid-state relay, an electromechanical relay, an optical switch, a DC-DC converter, and/or the like.

Although one switching device 180 is illustrated, the sanitizing system 100 may include multiple switching devices 180 that are independently controlled by the control unit 170. For example, each UV lamp 120 may be electrically connected to a different switching device 180 to enable independent control over each UV lamp 120. Alternatively, multiple UV lamps 120 located within the same general area can be electrically connected to the same switching device 180 which enables control over all of the multiple UV lamps 120 in that general area by actuating the single switching device 180. One or more of the switching devices 180 may enable variable control over the amount of power supplied to the associated UV lamps 120, besides merely turning the lamps 120 ON (e.g., active and emitting UV light) and OFF (e.g., inactive and not emitting UV light). For example, at least one switching device 180 can be controlled to supply full power to the associated UV lamps 120 and one or more reduced power levels, such as a medium power level and a low, non-zero power level.

In an embodiment, the UV light emitted by the UV lamps 120 is controlled to enable the occupants (e.g., passengers and crew) to be exposed to the UV light for a prolonged period of time without harm. For example, the emitted UV light may have a designated wavelength or a narrow band of wavelengths experimentally determined to be harmless to human tissue through prolonged exposure. Thus, even if the UV lamps 120 persistently emit UV light through the duration of the flight, the passengers would be unharmed. The UV lamps 120 may be configured or constructed to only generate the designated wavelength or the narrow band. Alternatively, a filter may be utilized that absorbs or dissipates wavelengths outside of the designated wavelength or the narrow band such that emitted UV light in the field of illumination only consists of the designated wavelength or the narrow band.

In a non-limiting example, the designated wavelength is 222 nm. It has been found that sanitizing UV light having a wavelength of 222 nm kills pathogens (such as viruses and bacteria), instead of inactivating pathogens. In contrast, UVC light at a wavelength of 254 nm inactivates pathogens by interfering with their DNA, resulting in temporary inactivation, but may not kill the pathogens. Instead, the pathogen may be reactivated by exposure to ordinary white light at a reactivation rate of about 10% per hour. As such, UVC light at a wavelength of 254 nm may be ineffective in illuminated areas, such as within an internal cabin of a vehicle. Moreover, UVC light at 254 nm is not recommended for human exposure because it may be able to penetrate human cells. In contrast, sanitizing UV light having a wavelength of 222 nm is safe for human exposure and kills pathogens. Further, the sanitizing UV light having a wavelength of 222 nm may be emitted at full power within one millisecond or less of the UV lamps 120 being activated (in contrast the UVC light having a wavelength of 254 nm, which may take seconds or even minutes to reach full power).

The input device 174 can represent or include a selector knob, a workstation computer, a tablet computer, a handheld computer (e.g., a smartphone), a keyboard, a touchpad, a joystick, and the like for enabling a pilot or another operator to control the sanitizing system 100. For example, an operator can enter a user input via the input device 174 for turning the UV lamps 120 ON and OFF and for selecting a power setting for one or more of the UV lamps 120. The output device 176 can be an integrated display device onboard the aircraft and/or a display screen on a personal computer, tablet, or handheld computer (e.g., smartphone).

The control unit 170 may generate control signals for controlling the output device 176 to display a notification indicating the operating status of the sanitizing system 100. The operating status can include whether the sanitizing system 100 is ON or OFF and the power setting or level of the UV lamps 120. The operating status represents the status of different subgroups that may be operating at different power settings. For example, the operating status may show that a UV lamp 120 in the lavatory is OFF while the UV lamps 120 in the PSUs above the passenger seats are ON.

Figure 4:
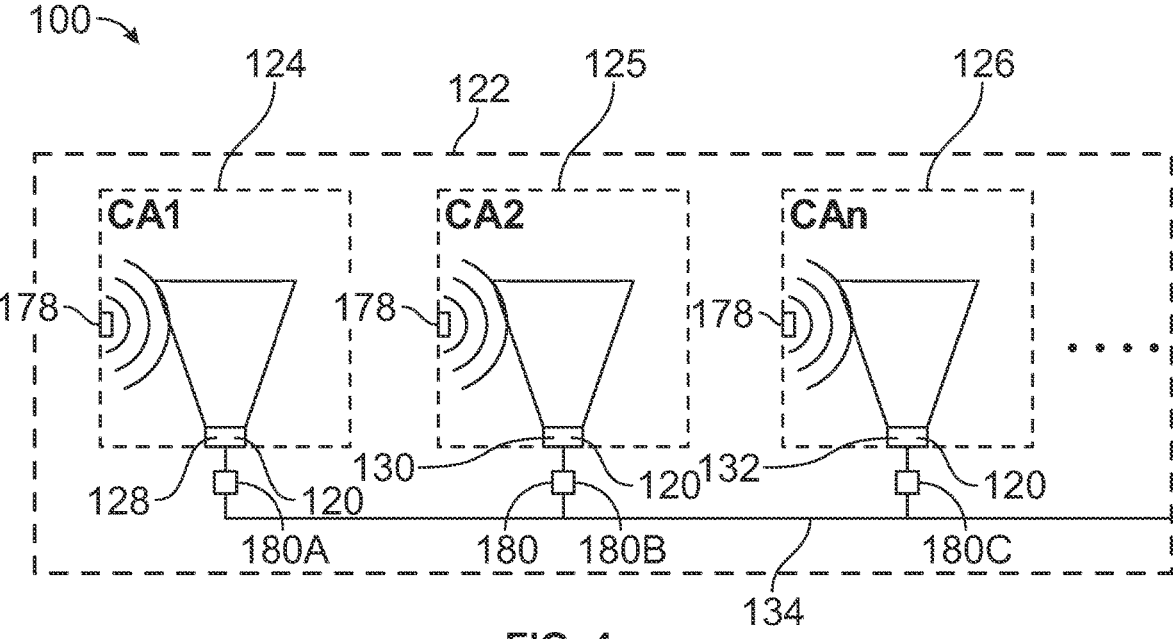
FIG. 4 is a schematic diagram showing the sanitizing system within an internal cabin of a vehicle according to an embodiment.

FIG. 4 is a schematic diagram showing the sanitizing system 100 within an internal cabin 122 of a vehicle according to an embodiment. The internal cabin 122 has multiple common areas 126. FIG. 4 shows a first common area 124 ("CA1"), a second common area 125 ("CA2"), and at least a third common area 126 ("CAn"), indicating that there may be more than three common areas 124-126. Each of the common areas 124-126 can represent a lavatory, an area immediately outside of a lavatory, a galley, an aisle, a crew quarters, a divider assembly between two different zones of the internal cabin 122, or an area adjacent an entrance to the vehicle. With reference to FIG. 2A, the common areas 124-126 may be the lavatories 45, the areas immediately outside of the lavatories 45, the aisles 50, 52, the galley 38, egress paths or door passageway areas 60 adjacent to the entrance to the aircraft, divider assemblies 48 between zones, doors 62, and/or the like. With reference to FIG. 2B, the common areas 124-126 may be the doors 92, door passageway areas 90, the aisle 84, the lavatory 87, and/or the like.

The sanitizing system 100 includes a first subset 128 of one or more UV lamps 120 in the first common area 124, a second subset 130 of one or more UV lamps 120 in the second common area 125, and a third subset 132 of one or more UV lamps 120 in the third common area 126. Each of the subsets 128, 130, 132 of UV lamps 120 emits UV light into the respective common area 124-126 to sanitize and disinfect air and surfaces within that common area 124-126.

The UV lamps 120 in the subsets 128, 130, 132 are electrically connected to a common bus 134 through which electrical power is supplied by the power source 172 (shown in FIG. 3). In the illustrated embodiment, switching devices 180 (e.g., 180A, 180B, 180C) are disposed between the bus 134 and each of the different subsets 128, 130, 132 of UV lamps 120. The control unit 170 (shown in FIG. 3) can independently control operation of the UV lamps 120 in the different common areas 124-126 via the switching devices 180A, 180B, 180C. For example, the control unit 170 can turn OFF the UV lamps 120 in the first common area 124 by generating a control signal to the switching device 180A that opens or blocks the conductive path from the bus 134 to the first subset 128 of UV lamps 120. The control unit 170 can also utilize the switching devices 180A, 180B, 180C to vary the power levels supplied to different subsets 128, 130, 132 of UV lamps 120 at a given time, such that the first subset 128 can receive a higher power level and the second subset 130 can receive a lower, reduced power level during a common time period. Modifying the power level supplied to the UV lamps 120 changes the intensity and/or range of the UV light emitted from the UV lamps 120, which affects the dose of UV radiation that is emitted per unit time. The dose is indicative of the amount or percentage of pathogens that can be killed or neutralized by the UV light.

The sanitizing system 100 includes at least one sensor 178 associated with each of the common areas 124-126. The sensors 178 monitor the common areas 124-126, and the signals generated by the sensors 178 are used to determine occupancy of the common areas 124-126, such as if any person is present in each of the common areas 124-126 at any given moment. The sensors 178 may be pressure sensors, proximity sensors, motion sensors, or the like. For example, pressure sensors can be installed under the floor in a common area 124-126 to detect a person walking in the common area 124-126. In another example, motion sensors can be installed on a door of a common area 124-126, such as a lavatory, to indicate when the door is open and closed. Other motion sensors can detect movement of people in the common area by tracking different positions of the people over time. One or more motion sensors may be optical sensors that detect motion when an optical beam is interrupted, which may occur as a person enters and leaves a room. The proximity sensors can utilize infrared and/or microwaves to determine when a person is within a designated proximity of the sensors. The sensors 178 can generate signals that are transmitted to the control unit 170 periodically at regular intervals or irregularly in response to detected monitoring variations, such as the optical beam being interrupted. The sensor signals can identify the source of the signals, such as the individual sensors that generate each of the signals.

The control unit 170 receives the signals from the sensors 178 and analyzes the signals to determine the occupancy of each of the common areas 124-126. For example, if a person is within a designated proximity of the proximity sensor 178 within the first common area 124, the control unit 170 determines, based on the sensor signal from that proximity sensor 178, that the first common area 124 is occupied. Once there is no longer person within the designated proximity, signals generated by the proximity sensor 178 are analyzed by the control unit 170 to determine that the common area 124 is unoccupied.

Figures 5, 6:
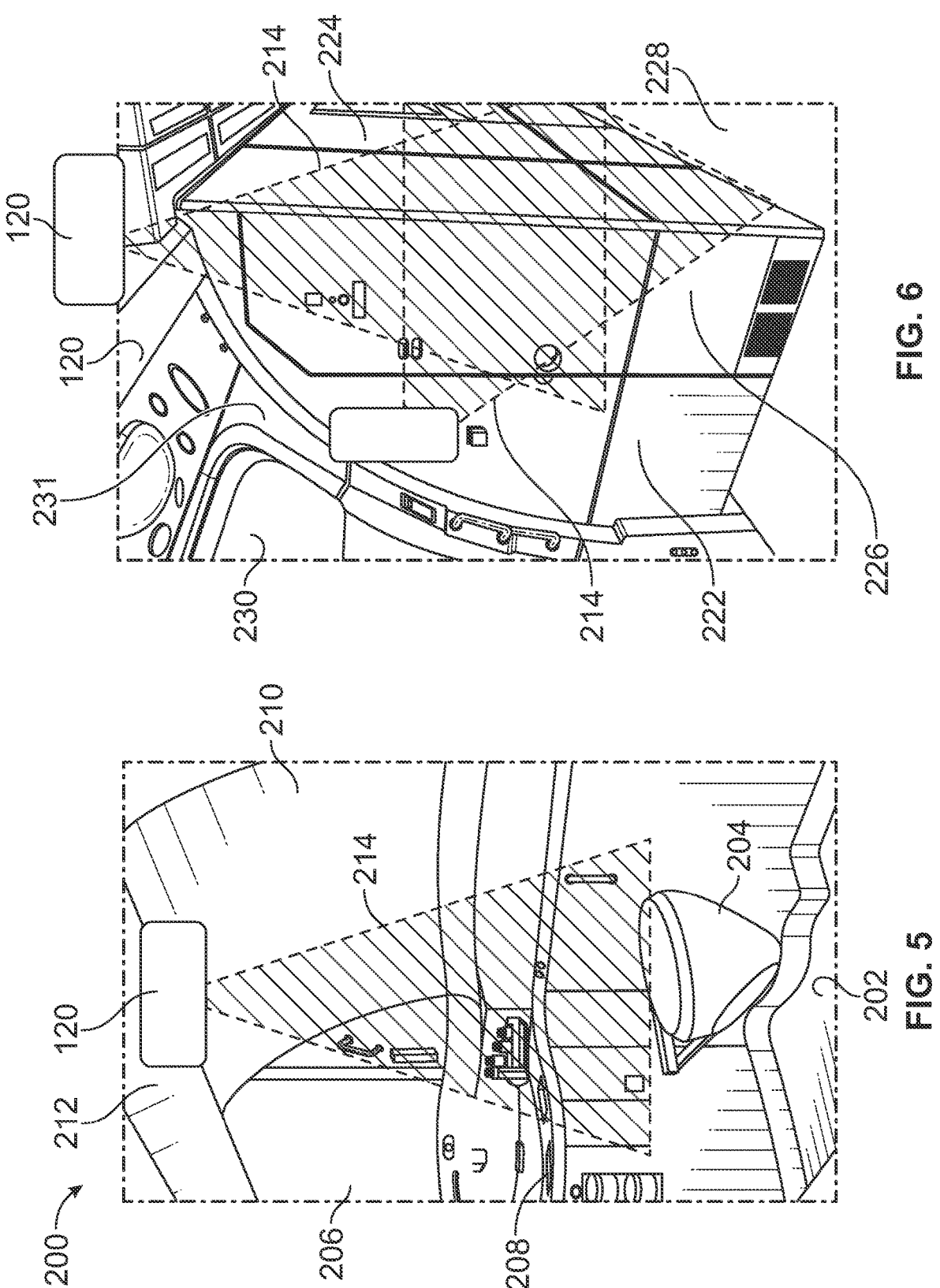
FIG. 5 illustrates a perspective internal view of a lavatory within an internal cabin of a vehicle.
FIG. 6 illustrates a perspective view of an area immediately outside of a lavatory within an internal cabin of a vehicle.

FIG. 5 illustrates a perspective internal view of a lavatory 200 within an internal cabin of a vehicle, such as any of the internal cabins described herein. For example, the lavatory 200 may be any of the lavatories 45 shown in FIG. 2A or the lavatory 87 shown in FIG. 2B. The lavatory 200 is an example of an enclosed, common area within the internal cabin that is available to the passengers onboard the vehicle. The lavatory 200 may represent one of the common areas 124-126 shown in FIG. 4. The lavatory 200 includes a floor 202, a toilet 204, a mirror 206, a sink 208, walls 210, a ceiling 212, and a door (not shown) for establishing privacy. A UV lamp 120 of the sanitizing system 100 is located within the lavatory 200. The UV lamp 120 is configured to emit UV light into the lavatory 200 to sanitize the air and surfaces. The UV light is transmitted in a field of illumination 214, which refers to a three-dimensional volume in space that is defined by the propagation of UV light waves (e.g., rays) emitted by the UV lamp 120. The width of the field of illumination can depend on mechanical features of the UV lamp 120, such as reflectors, collimators, lenses, and the like, and optionally may be set to provide a predetermined width. Although not shown in FIG. 5, one or more of the sensors 178 of the sanitizing system 100 may be disposed within the lavatory 200, such as mounted to a wall 210, under the floor 202, on the ceiling 212, or on the door.

FIG. 6 illustrates a perspective view of an area 220 immediately outside of a lavatory within an internal cabin of a vehicle, such as any of the internal cabins described herein. The area 220 is an example of a common area within the internal cabin that is available to the passengers onboard the vehicle. The area 220 may represent one of the common areas 124-126 shown in FIG. 4. The area 220 includes a first wall 222 and a second wall 224 that extends from the first wall 222 at a transverse angle, such as orthogonal. A door 226 to the lavatory is mounted along the first wall 222. The second wall 224 extends along an aisle 228 that leads towards passenger seats (not shown). Optionally, the area 220 may also represent an area adjacent to an entrance to the vehicle. For example, a vehicle door 230 is located on a fuselage wall 231 adjacent to the first wall 222. The first wall 222 may be between the vehicle door 230 and the second wall 224. Passengers may occupy and traverse the area 220 when boarding the vehicle through the vehicle door 230, when entering the lavatory, when waiting to enter the lavatory, when exiting the lavatory, and/or when deboarding the vehicle.

In the illustrated embodiment, two UV lamps 120 of the sanitizing system 100 are located within the area 220 and positioned to emit UV light into the area 220. One of the UV lamps 120 is mounted along a ceiling 232 of the area 220, and the other UV lamp 120 is mounted on the fuselage wall 231 or the first wall 222. The fields of illumination 214 of the two UV lamps 120 may partially overlap within the area 220. Although not shown, one or more of the sensors 178 of the sanitizing system 100 are disposed within the area 220, such as mounted to first wall 222, the fuselage wall 231, the ceiling 232, or the like, to monitor occupancy within the area 220.

Figure 7:
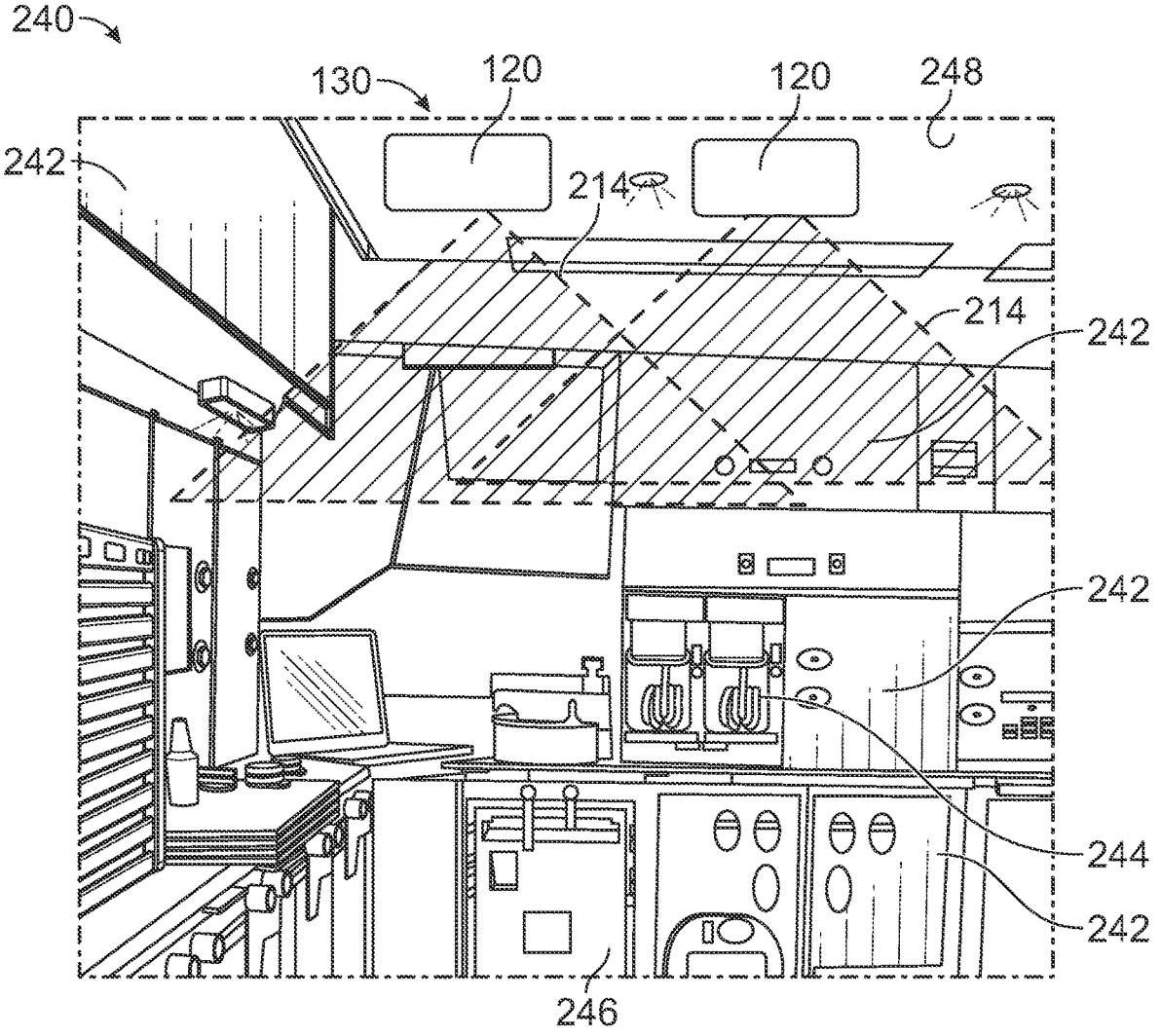
FIG. 7 illustrates a perspective view of a galley within an internal cabin of a vehicle.

FIG. 7 illustrates a perspective view of a galley 240 within an internal cabin of a vehicle, such as any of the internal cabins described herein. The galley 240 is an example of a common area within the internal cabin that is available to the passengers onboard the vehicle. The galley 240 may represent one of the common areas 124-126 shown in FIG. 4. The galley 240 includes various cabinets 242 and appliances, such as a coffee maker 244. The galley 240 also includes a galley cart 246. The galley 240 may be occupied by crew members when preparing food and drinks for passengers, disposing of trash, and the like. Some crew members may sit in the galley during takeoff and landing stages of a trip. Passengers walk through or past the galley during boarding and deboarding.

In the illustrated embodiment, two UV lamps 120 of the sanitizing system 100 are located within the galley 240 and positioned to emit UV light into the galley 240. Both UV lamps 120 are mounted along a ceiling 248 of the galley 240. The UV lamps 120 may be spaced apart such that the fields of illumination 214 of the two UV lamps 120 partially overlap to provide substantial coverage of the galley 240. Although not shown, one or more of the sensors 178 of the sanitizing system 100 are disposed within the galley 240, such as mounted to the ceiling 248, along a floor of the galley 240, to the cabinets 242, and/or the like, to monitor occupancy within the galley 240.

FIG. 8 illustrates a side view of a passenger seating area 260 of an internal cabin showing a group 262 of passenger seats 264 on one side of an aisle 266. The internal cabin is within a vehicle and can be any of the internal cabins described herein. The aisle 266 in the passenger seating area 260 is an example of a common area that is available to the passengers and crew onboard the vehicle. The aisle 266 may represent one of the common areas 124-126 shown in FIG. 4. The passenger seating area 260 also includes stowage compartments 268 for storing carry-on passenger luggage. The stowage compartments 268 may be located above the seats 264. A ceiling 270 is located above the aisle 266. The passengers can occupy the aisle 266 when walking to their seats 264 and walking away from their seats 264, such as during boarding and deboarding and trips to the lavatory.

In the illustrated embodiment, three UV lamps 120 of the sanitizing system 100 are located within the region of the aisle 266. For example, the UV lamps 120 are mounted to the ceiling 270 above the aisle 266 and positioned to emit UV light towards the aisle 266. The UV lamps 120 may be spaced apart along a length of the aisle 266 at a designated spacing that enables the fields of illumination 214 of adjacent UV lamps 120 to partially overlap above the aisle 266 to provide substantial sanitization coverage of the aisle region. In the illustrated embodiment, multiple sensors 178 of the sanitizing system 100 are disposed within the aisle region and spaced apart along the length of the aisle 266. For example, the sensors 178 may be mounted on or under the floor 272 of the aisle 266 to monitor occupancy of the aisle 266. The sensors 178 may be pressure sensors mounted under the floor 272 to monitor occupants walking on the floor 272 based on the force of footsteps on the floor 272.

In an embodiment, the sensors 178 may align with different corresponding UV lamps 120 along the length of the aisle 266 which enables tracking a person walking along the aisle 266 based on the order in which the sensors 178 detect footsteps of the person. The control unit 170 (shown in FIG. 3) optionally can vary the power supplied to different UV lamps 120 along the aisle 266 at a given time based on the tracked movement of a person on the aisle 266. As described in more detail below, the control unit 170 can effectively partition the aisle 266 into different segments 274 along the length. Once a person passes beyond a first segment 274A, the control unit 170 can increase the power supplied to the UV lamp 120 in the first segment 274 to increase the intensity and/or range of the UV light emitted by that UV lamp 120 to rapidly sanitize the area just occupied by the person walking the aisle 266. The control unit 170 subsequently increases the power supplied to an adjacent UV lamp 120 in the direction that the person is walking after the person passes beyond the adjacent segment 274. After a designated amount of time, the control unit 170 reduces the power supplied to the UV lamps 120 to conserve energy. As a result, the sensors 178 enable the control unit 170 to operate the UV lamps 120 in sequence to track movement of people along the aisle 266, killing or neutralizing pathogens emitted by the people as they walk along the aisle 266. The control unit 170 can also use the tracked movement of a person to begin the rapid (high power level) sanitation while the person is still in the segment 274, which can kill pathogens before the pathogens can be breathed or encountered by the person.

FIG. 9 illustrates a side view of one of the UV lamps 120 of the sanitizing system 100 according to an embodiment. The UV lamp 120 includes a housing 150, a bulb 152, a cover sheet 154 or lens, and a reflector 156. The bulb 152 and the reflector 156 are held within a cavity 158 defined by the housing 150 and the cover sheet 154. The bulb 152 emits UV light that penetrates through the cover sheet 154, which is transparent or at least translucent, into the field of illumination 214. The bulb 152 may be an excimer bulb. The reflector 156 is reflective and arranged such that the bulb 152 is between the reflector 156 and the cover sheet 154. The reflector 156 is shaped and positioned to reflect light that impinges on the surface of the reflector 156 towards the cover sheet 154. The reflector 156 may be curved at least partially around the bulb 152. The walls of the housing 150 may be opaque, and optionally reflective, to prevent light transmission through the walls, ensuring that the field of illumination 214 is defined by light transmitted through the cover sheet 154. The UV lamp 120 may include additional components, such as a convex lens or a concave lens, hardware for mounting the bulb 152 to the housing 150, and circuitry for supplying electrical power to the bulb 152.

In an embodiment, the field of illumination 214 is static and consistent during operation of the UV lamp 120. For example, the reflector 156 may be mounted in a fixed position within the housing 150. In an alternative embodiment, the reflector 156 may be able to rotate or swivel to change the dimensions of the field of illumination 214.

FIG. 10 illustrates a side view of one of the UV lamps 120 of the sanitizing system 100 according to another embodiment. The reflector 156 is coupled to an actuator that is controlled to swivel and/or translate the reflector 156 to change the angle of the reflector 156 relative to the bulb 152 and the cover sheet 154. In the illustrated position, the reflector 156 is off-center to the right and the field of illumination 214 (shown in solid lines) is skewed to the left. As the reflector 156 is gradually moved to a position off-center to the left, the field of illumination 214 (not shown) shifts to the right. As a result, over multiple cycles, the UV light is transmitted into a wider illumination coverage area 160 than the static lamp 120 shown in FIG. 9. The illumination coverage area 160 represents the outermost edges of the field of illumination 214 through a full cycle of the moving reflector 156, such that the dashed line represents an edge when the reflector 156 is off-center to the left. In another embodiment, the wider illumination coverage area 160 can be provided by swiveling or rotating the entire housing 150 or a lens within the housing instead of moving the reflector 156.

Figure 11:
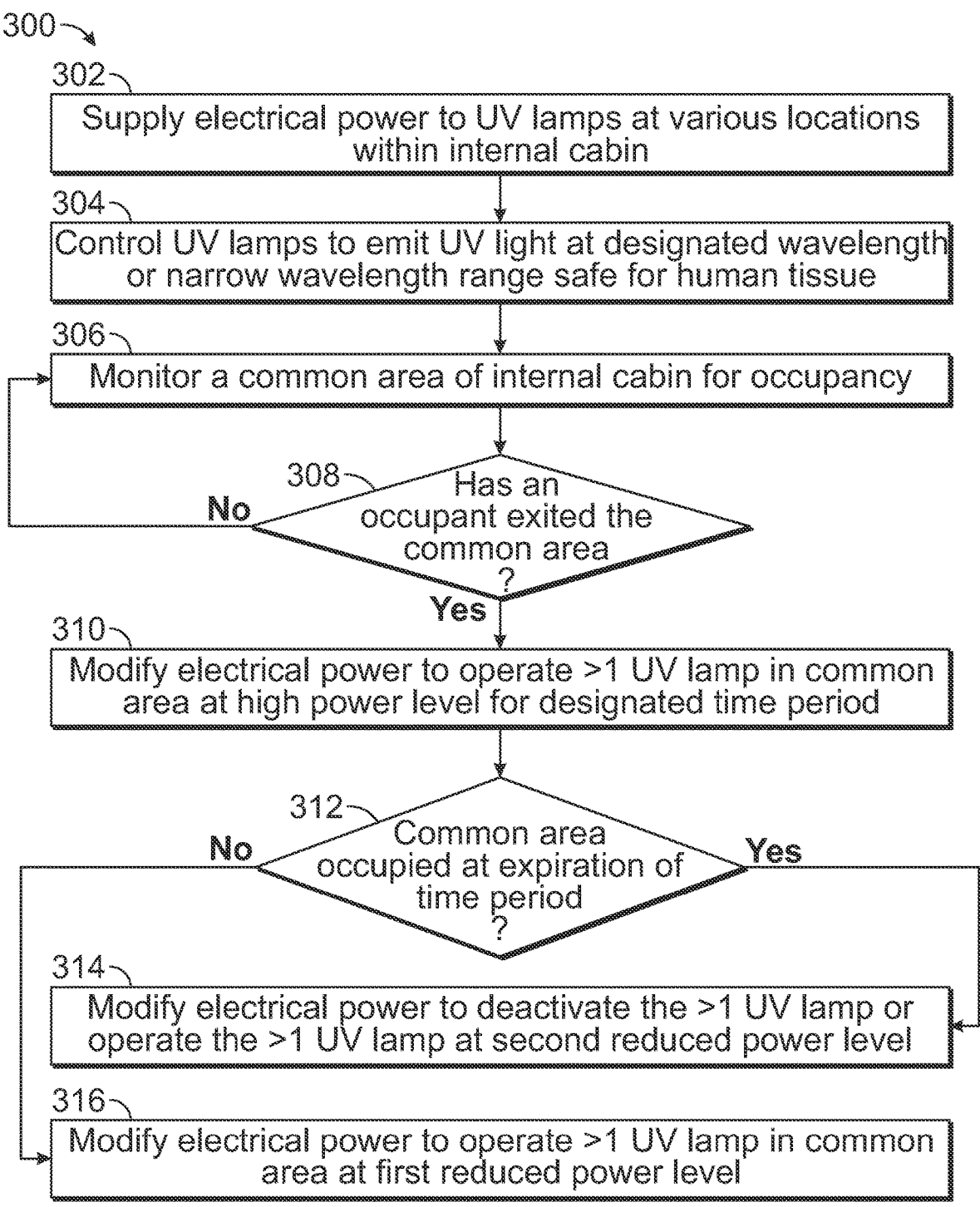
FIG. 11 is a flow chart of a method for sanitizing and disinfecting air and surfaces within an internal cabin of a vehicle.

FIG. 11 is a flow chart of a method 300 for sanitizing and disinfecting air and surfaces within an internal cabin of a vehicle. The method 300 is particularly applicable to sanitizing common areas that may be trafficked by multiple passengers and/or crew members. The method 300 may be performed by the sanitizing system 100 described above with reference to FIGS. 1-10. Certain steps of the method 300 may be performed by the control unit 170 shown in FIG. 3 based on programmed logic or instructions. The method 300 optionally includes additional steps than described, fewer steps than described, and/or different steps than described.

At 302, electrical power is supplied to UV lamps 120 at various locations within an internal cabin 122 of a vehicle. The electrical power can be supplied by an onboard power source 172, such as a generator. At 304, the UV lamps 120 are controlled to emit UV light into the internal cabin 122 during a trip of the vehicle at a designated wavelength or a narrow wavelength range that is safe for human tissue. The designated wavelength may be 222 nm. At 306, a common area 126 of the internal cabin 122 is monitored for occupancy of the common area 126. The common area 126 can be a lavatory, an area immediately outside of the lavatory, a galley, an aisle, a crew quarters, a dividing area between two different zones of the internal cabin, or an area adjacent an entrance to the vehicle. The occupancy can be monitored via the use of one or more sensors 178 mounted to detect the presence of a person in the common area 126.

At 308, a determination is made whether an occupant of the common area 126 has exited the common area 126. For example, signals from the sensors 178 can be analyzed to determine when an occupied common area 126 becomes no longer occupied, at least temporarily. This may occur when a person in a lavatory exits the lavatory through the door, for example. If it is determined that the occupant has exited the common area 126, flow proceeds to 310. At 310, the electrical power supplied to one or more UV lamps 120 in the common area 126 is increased such that the one or more UV lamps 120 in the common area 126 are operated at a high power level for a designated time period. The high power level is a relative term, but refers to a power level that causes the UV lamps 120 to emit UV light at an intensity and/or range that provides rapid sanitization of the common area 126. The high power level may represent 80%, 90%, 95%, 100% or the like, of the rated power of the UV lamps 120. The UV lamps 120 may be operated at a lower power level while the occupant is within the common area 126, unless the occupant enters the common area 126 within the designated time period after a previous occupant exited the common area 126, as described below. The designated time period is application-specific, and generally refers to a minimum amount of time that is needed to deliver a desired dose of UV radiation into the common area 126 for rapidly killing or neutralizing pathogens in the air and on surfaces. The designated time period may be based on the size of the common area 126, the number of UV lamps 120 in the common area 126, and the power output of the UV lamps 120 at the high power level. In non-limiting examples, the designated time period may be 10 seconds, 20 seconds, 30 seconds, 45 seconds, or 1 minute. If, on the other hand, the occupant has not exited the common area 126, the method 300 returns to 306 for continued monitoring of the common area 126.

At 312, at the expiration of the designated time period, as the UV lamps 120 in the common area 126 are operated at the high power level, another determination is made whether the common area 126 is occupied. If the common area 126 is occupied by another person at the expiration of the time period, then flow proceeds to 314. At 315, the electrical power supplied to the one or more UV lamps 120 in the common area 126 is modified to operate the UV lamps 120 at a first reduced power level that is less than the high power level. The first reduced power level may be classified as a medium power level or a low power level. The UV lamps 120 continue to emit UV light, but the UV light has less intensity and/or range than the UV light emitted during the designated time period. The UV lamps 120 therefore may continue to sanitize the common area 126 while occupied by another person.

On the other hand, if the common area 126 is not occupied at the expiration of the time period, the method 300 proceeds to 316. At 316, the electrical power supplied to the one or more UV lamps 120 in the common area 126 is modified to either deactivate the UV lamps 120 in the common area 126 or operate the UV lamps 120 at a second reduced power level. For example, the UV lamps 120 may be turned off to cease emitting UV light into the common area 126 until another occupant of the common area 126 exits the common area 126. Alternatively, the UV lamps 120 may be kept on and emitting UV light at the second reduced power level, which may be less than the high power level and the first reduced power level. For example, the second reduced power level may be a low power level, also referred to as a maintenance level (and the first reduced power level may be a medium power level). After step 314 or 316, the method 300 returns to 306 to continue monitoring the common area 126 for occupancy. Modulating the electrical power supplied to (e.g., consumed by) the UV lamps 120 in the common areas 126 of an internal cabin 122 to provide short bursts of high intensity UV light based on occupancy can be used to kill pathogens in an energy efficient manner.

In an alternative embodiment of the method 300, at the expiration of the designated time period following step 310, the method 300 essentially jumps directly to step 316. For example, regardless of whether or not the common area 126 is occupied, after the designated time period ends the UV lamps 120 in the common area 120 are either deactivated or operated at a reduced (e.g., low) power level and flow returns to 306. The UV lamps 120 are kept off or at the reduce power level until it is determined at 308 that a subsequent occupant has exited the common area 126 such that the method returns to 310.

As described herein, embodiments of the present disclosure provide systems and methods for sanitizing and disinfecting surfaces, air, and people within an internal cabin of a vehicle, particularly in high trafficked common areas, using UV light without harming the people exposed to the UV light. Further, embodiments of the present disclosure provide built-in, easy-to-use, and safe systems and methods for using UV light to sanitize air and surfaces within an internal vehicle cabin, and modulating the power draw of the UV lights to conserve energy.

Further, the disclosure comprises embodiments according to the following clauses:

Clause 1. A sanitizing system comprising:

a plurality of ultraviolet (UV) lamps mounted at various locations within an internal cabin of a vehicle, wherein the UV lamps are configured to receive electrical power from a power source onboard the vehicle and to emit UV light into the internal cabin during a trip of the vehicle; and a control unit including one or more processors and operatively connected to the UV lamps, the control unit configured to modify the electrical power supplied to one or more of the UV lamps located in a common area of the internal cabin based on occupancy of the common area.

Clause 2. The sanitizing system of Clause 1, wherein, responsive to detecting that an occupant of the common area has exited the common area, the control unit is configured to operate the one or more UV lamps located in the common area at a high power level for a designated time period to provide rapid sanitization of the common area.

Clause 3. The sanitizing system of Clause 2, wherein, responsive to detecting that the common area is occupied at an expiration of the designated time period, the control unit is configured to operate the one or more UV lamps located in the common area at a reduced power level that is less than the high power level.

Clause 4. The sanitizing system of Clause 3, wherein the reduced power level is a medium power level that is less than the high power level and greater than a low, non-zero power level.

Clause 5. The sanitizing system of Clause 2, wherein, responsive to detecting that the common area is not occupied at an expiration of the designated time period, the control unit is configured to one of (i) turn off the one or more UV lamps located in the common area to cease emitting UV light, or (ii) operate the one or more UV lamps located in the common area at a reduced power level that is less than the high power level.

Clause 6. The sanitizing system of Clause 5, wherein the reduced power level is a low, non-zero power level.

Clause 7. The sanitizing system of any of Clauses 1-6, wherein the common area is one of a lavatory, an area immediately outside of the lavatory, a galley, an aisle, a crew quarters, a divider assembly between two different zones of the internal cabin, or an area adjacent an entrance to the vehicle.

Clause 8. The sanitizing system of any of Clauses 1-7, further comprising one or more sensors mounted within the internal cabin and operatively connected to the control unit, the one or more sensors configured to monitor the common area, the control unit configured to determine the occupancy of the common area based on signals received from the one or more sensors.

Clause 9. The sanitizing system of Clause 8, wherein the one or more sensors include at least one of a pressure sensor, a proximity sensor, or a motion sensor.

Clause 10. The sanitizing system of any of Clauses 1-9, wherein the one or more sensors include multiple sensors and at least a subset of the sensors are pressure sensors disposed under a floor of the internal cabin to monitor occupants walking on the floor.

Clause 11. The sanitizing system of any of Clauses 1-10, wherein the UV lamps are configured to emit the UV light at a designated wavelength or narrow wavelength range that is safe for human tissue.

Clause 12. The sanitizing system of Clause 11, wherein the designated wavelength is 222 nm.

Clause 13. The sanitizing system of any of Clauses 1-12, wherein the vehicle is an aircraft.

Clause 14. A method comprising:

supplying electrical power from a power source onboard a vehicle to a plurality of ultraviolet (UV) lamps mounted at various locations within an internal cabin of the vehicle for the UV lamps to emit UV light into the internal cabin during a trip of the vehicle; and modifying the electrical power supplied to one or more of the UV lamps located in a common area of the internal cabin based on occupancy of the common area.

Clause 15. The method of Clause 14, further comprising:

monitoring the common area for occupancy via one or more sensors, and responsive to detecting that an occupant of the common area has exited the common area, the modifying of the electrical power supplied to the one or more UV lamps in the common area includes operating the one or more UV lamps at a high power level for a designated time period to provide rapid sanitization of the common area.

Clause 16. The method of Clause 15, wherein, responsive to detecting that the common area is occupied at an expiration of the designated time period, the modifying of the electrical power supplied to the one or more UV lamps in the common area includes operating the one or more UV lamps at a first reduced power level that is less than the high power level.

Clause 17. The method of Clause 16, wherein, responsive to detecting that the common area is not occupied at the expiration of the designated time period, the modifying of the electrical power supplied to the one or more UV lamps in the common area includes one of (i) turning off the one or more UV lamps located in the common area to cease emitting UV light, or (ii) operating the one or more UV lamps at a second reduced power level that is less than the first reduced power level.

Clause 18. The method of any of Clauses 14-17, further comprising controlling the UV lamps to emit the UV light at a designated wavelength or narrow wavelength range that is safe for human tissue at prolonged exposure.

Clause 19. The method of any of Clauses 14-18, wherein the common area is one of a lavatory, an area immediately outside of the lavatory, a galley, an aisle, a crew quarters, a dividing area between two different zones of the internal cabin, or an area adjacent an entrance to the vehicle.

Clause 20. A sanitizing system comprising:

a plurality of ultraviolet (UV) lamps mounted at various locations within an internal cabin of a vehicle, wherein the UV lamps are configured to receive electrical power from a power source onboard the vehicle and to emit UV light into the internal cabin during a trip of the vehicle at a designated wavelength or narrow wavelength range that is safe for human tissue;

one or more sensors mounted within the internal cabin and configured to monitor a common area of the internal cabin; and a control unit including one or more processors and operatively connected to the UV lamps and the one or more sensors, the control unit configured to determine an occupancy of the common area based on signals received from the one or more sensors and to modify the electrical power supplied to one or more of the UV lamps located in the common area based on the determined occupancy of the common area While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

As used herein, value modifiers such as "about," "substantially," and "approximately" inserted before a numerical value indicate that the value can represent other values within a designated threshold range above and/or below the specified value, such as values within 5%, 10%, or 15% of the specified value.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects.

Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing system comprising:
ultraviolet (UV) lamps mounted at various locations within common areas of an internal cabin of a vehicle, wherein the UV lamps are configured to receive electrical power from a power source onboard the vehicle and to emit UV light into the internal cabin during a trip of the vehicle; and
a control unit including one or more processors and operatively connected to the UV lamps, the control unit configured to:
supply the electrical power to the UV lamps located in the common areas of the internal cabin to activate the UV lamps at a full power level based on the occupancy of the common areas,
stop supply of the electrical power to deactivate the UV lamps located in the common areas of the internal cabin based on the occupancy of the common areas,
modify the electrical power supplied to one or more of the UV lamps located in the common areas of the internal cabin based on occupancy of the common areas, wherein the electrical power supplied to the one or more of the UV lamps is modified to operate the one or more of the UV lamps at (a) a first reduced power level that is a non-zero power level that is less than the full power level, and (b) a second reduced power level that is also a non-zero power level that is less than both the first reduced power level and the full power level,
operate the one or more of the UV lamps at one or both of the first reduced power level or the second reduced power level when one or more of the common areas is occupied, and
operate the one or more of the UV lamps at the full power after the one or more of the common areas is occupied for a designated period of time.

2. The sanitizing system of claim 1, wherein, responsive to detecting that an occupant of one of the common areas has exited the one of the common areas, the control unit is configured to operate the UV lamps located in the common area at the full power level for a designated time period to provide sanitization of the one of the common areas.

3. The sanitizing system of claim 2, wherein, responsive to detecting that the one of the common areas is occupied at an expiration of the designated time period, the control unit is configured to operate the UV lamps located in the one of the common areas at one of the first reduced power level or the second reduced power level.

4. The sanitizing system of claim 2, wherein, responsive to detecting that the one of the common areas is not occupied at an expiration of the designated time period, the control unit is configured to turn off the UV lamps located in the one of the common areas to cease emitting UV light after operating the UV lamps located in the one of the common areas at the first reduced power level and the second reduced power level.

5. The sanitizing system of claim 1, wherein the common areas includes a lavatory, an area immediately outside of the lavatory, a galley, an aisle, a crew quarters, a divider assembly between two different zones of the internal cabin, and an area adjacent an entrance to the vehicle.

6. The sanitizing system of claim 1, further comprising sensors mounted within the internal cabin and operatively connected to the control unit, the sensors configured to monitor the common areas, the control unit further configured to determine the occupancy of the common areas based on signals received from the sensors.

7. The sanitizing system of claim 6, wherein the sensors include at least one of a pressure sensor, a proximity sensor, or a motion sensor.

8. The sanitizing system of claim 1, wherein at least a subset of the sensors are pressure sensors disposed under a floor of the internal cabin to monitor occupants walking on the floor.

9. The sanitizing system of claim 1, wherein the UV lamps are configured to emit the UV light at a designated wavelength that is safe for human tissue.

10. The sanitizing system of claim 9, wherein the designated wavelength is 222 nm.

11. The sanitizing system of claim 1, wherein the vehicle is an aircraft.

12. The sanitizing system of claim 1, wherein one or more of the UV lamps are configured to persistently emit the UV light into the internal cabin during a duration of the trip of the vehicle.

13. The sanitizing system of claim 1, wherein the control unit is configured to operate the one or more of the UV lamps at the full power when one or more of the common areas is occupied.

14. The sanitizing system of claim 1, wherein the control unit is configured to modify operation of the one or more of the UV lamps between a deactivated state, the first reduced power level, the second reduced power level, and the full power level.

15. A method for a sanitizing system comprising:
ultraviolet (UV) lamps mounted at various locations within common areas of an internal cabin of a vehicle, wherein the UV lamps are configured to receive electrical power from a power source onboard the vehicle and to emit UV light into the internal cabin during a trip of the vehicle; and
a control unit including one or more processors and operatively connected to the UV lamps, the control unit configured to:
supply the electrical power to the UV lamps located in the common areas of the internal cabin to activate the UV lamps at a full power level based on the occupancy of the common areas,
stop supply of the electrical power to deactivate the UV lamps located in the common areas of the internal cabin based on the occupancy of the common areas,
modify the electrical power supplied to one or more of the UV lamps located in the common areas of the internal cabin based on occupancy of the common areas, wherein the electrical power supplied to the one or more of the UV lamps is modified to operate the one or more of the UV lamps at (a) a first reduced power level that is a non-zero power level that is less than the full power level, and (b) a second reduced power level that is also a non-zero power level that is less than both the first reduced power level and the full power level, operate the one or more of the UV lamps at one or both of the first reduced power level or the second reduced power level when one or more of the common areas is occupied, and operate the one or more of the UV lamps at the full power after the one or more of the common areas is occupied for a designated period of time, the method comprising:

supplying the electrical power to the UV lamps located in the common areas of the internal cabin to activate the UV lamps based on the occupancy of the common areas;

stopping supply of the electrical power to deactivate the UV lamps located in the common areas of the internal cabin based on the occupancy of the common areas; and modifying the electrical power supplied to the one or more of the UV lamps located in the common areas of the internal cabin based on the occupancy of the common areas.

16. The method of claim 15, further comprising monitoring the common areas for occupancy via sensors, and responsive to detecting that an occupant of one of the common areas has exited the one of the common areas, the modifying of the electrical power supplied to the UV lamps in the one of the common areas includes operating the UV lamps at one of the first reduced power level or the second reduced power level for a designated time period to provide sanitization of the one of the common areas.

17. The method of claim 15, wherein, responsive to detecting that the one of the common areas is not occupied at the expiration of the designated time period, the modifying of the electrical power supplied to the UV lamps in the one of the common areas includes turning off the UV lamps located in the one of the common areas to cease emitting UV light after operating the UV lamps at one or both of the first reduced power level or the second reduced power level.

18. The method of claim 15, further comprising controlling the UV lamps to emit the UV light at a designated wavelength that is safe for human tissue at prolonged exposure.

19. A sanitizing system comprising:

ultraviolet (UV) lamps mounted at various locations within common areas of an internal cabin of a vehicle, wherein the UV lamps are configured to receive electrical power from a power source onboard the vehicle and to emit UV light into the internal cabin during a trip of the vehicle at a designated wavelength that is safe for human tissue;

sensors mounted within the common areas of the internal cabin and configured to monitor the common areas of the internal cabin; and a control unit including one or more processors and operatively connected to the UV lamps and the sensors, the control unit configured to determine occupancy of the common areas based on signals received from the sensors and to:

supply the electrical power to the UV lamps located in the common areas of the internal cabin to activate the UV lamps at a full power level based on the determined occupancy of the common areas, stop supplying the electrical power supplied to deactivate the UV lamps located in the common areas of the internal cabin based on the determined occupancy of the common areas, modify the electrical power supplied to one or more of the UV lamps located in the common areas of the internal cabin based on the determined occupancy of the common areas, wherein the electrical power supplied to the one or more of the UV lamps is modified to operate the one or more of the UV lamps at (a) a first reduced power level that is a non-zero power level that is less than the full power level, and (b) a second reduced power level that is also a non-zero power level that is less than both the first reduced power level and the full power level, operate the one or more of the UV lamps at one or both of the first reduced power level or the second reduced power level when one or more of the common areas is occupied, and operate the one or more of the UV lamps at the full power after the one or more of the common areas is occupied for a designated period of time.

* * * * *